(12) United States Patent
Shiina et al.

(10) Patent No.: US 8,193,394 B2
(45) Date of Patent: Jun. 5, 2012

(54) PROCESS FOR PRODUCTION OF LASOFOXIFENE OR ANALOGUE THEREOF

(75) Inventors: Isamu Shiina, Tokyo (JP); Yoshiyuki Sano, Tokyo (JP); Kenya Nakata, Tokyo (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 366 days.

(21) Appl. No.: 12/162,068

(22) PCT Filed: Jan. 25, 2007

(86) PCT No.: PCT/JP2007/051186
§ 371 (c)(1),
(2), (4) Date: Aug. 8, 2008

(87) PCT Pub. No.: WO2007/086471
PCT Pub. Date: Aug. 2, 2007

(65) Prior Publication Data
US 2009/0012314 A1    Jan. 8, 2009

(30) Foreign Application Priority Data

Jan. 26, 2006 (JP) ................................. 2006-018079
Jan. 9, 2007 (JP) ................................. 2007-001114

(51) Int. Cl.
*C07C 33/02*  (2006.01)
(52) U.S. Cl. ...................................... 568/716; 568/718
(58) Field of Classification Search .................. 568/300, 568/716, 718
See application file for complete search history.

(56) References Cited

U.S. PATENT DOCUMENTS 3,919,327 A    11/1975   Lednicer

FOREIGN PATENT DOCUMENTS

| EP | 1 055 658 | 11/2000 |
|---|---|---|
| JP | H10-503215 | 3/1998 |
| JP | 11-349527 | 12/1999 |
| JP | 2000-327670 | 11/2000 |
| WO | WO 96/21656 | 7/1996 |

OTHER PUBLICATIONS

Document No. 131:322428 retrieved from CAPLUS, Jun. 2010.*
Document No. 97:55437 retrieved from CAPLUS, Jun. 2010.*
Anstead, et al. Journal of Medicinal Chemistry 1988, 31, 1316-1326.*
Isomers [online], [retrieved on Mar. 11, 2007]. Retrieved from the Internet, URL; http://chemed.chem.purdue.edu/genchem/topicreview/bp/1 organic/isomers.html>.*
Bindal, R. D., et al., "Utility of 4-Trimethylsiloxyphenylmagnesium Bromide in Grignard Reactions", Synthesis, May 1982, No. 5, p. 405-7.

Lednicer, D., et al., "Mammalian Antifertility Agents. VI. A Novel Sequence for the Preparation of 1,2-Disubstituted 3,4-Dihydronaphthalenes", Journal of Medicinal Chemistry, Sep. 1969, vol. 12, p. 881-5.
Anstead, G. M., et al., "2,3-Diarylindenes and 2,3-Diarylindenones: Synthesis, Molecular Structure, Photochemistry, Estrogen Receptor Binding Affinity, and Comparisons with Related Triarylethylenes", Journal of Medicinal Chemistry, 1988, vol. 31, No. 7, p. 1316-26.

(Continued)

*Primary Examiner* — Shawquia Young
(74) *Attorney, Agent, or Firm* — Scully, Scott, Murphy & Presser, P.C.

(57) ABSTRACT

Disclosed is a novel process for production of lasofoxifene, nafoxidine or an analogue thereof, which comprises reduced number of reaction steps, has a high efficiency, and is practically advantageous. For the production of lasofoxifene or an analogue thereof, a compound represented by the formula (4) is used as an intermediate. The compound represented by the formula (4) can be produced using compounds represented by the formulae (1) to (3) as starting compounds by performing the coupling of the three components in one step.

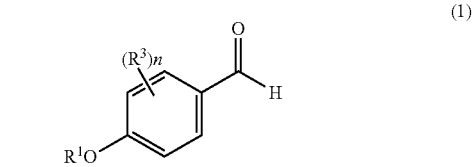

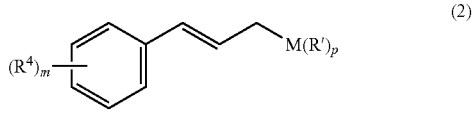

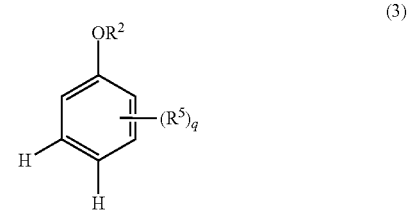

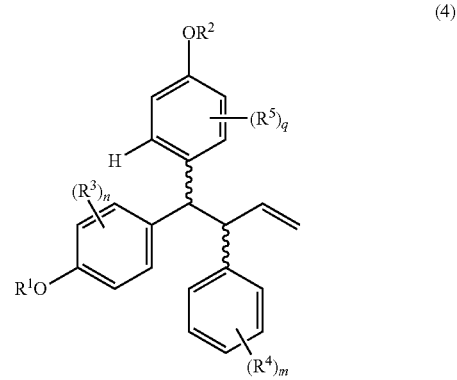

4 Claims, 2 Drawing Sheets

OTHER PUBLICATIONS

Bindal et al: "1,2-Bis(4-Hydroxyphenyl)-3,4-Dihydro-6-HY Droxynaphthalene, A Photofluorogenic Ligand for the Estrogen Receptor", Photochemistry and Photobiology, Wiley-Blackwell Publishing, Inc, US, Jan. 1, 1986, pp. 121-126, vol. 43, No. 2, XP000980188, ISSN: 0031-8655, DOI:10.1111/J,1751-1097.1986. TB09502.X.

Sano Yoshiyuki et al: "An expeditious synthesis of lasofoxifene and nafoxidine via the novel three-component coupling reaction", Chemistry Letters, Chemical Society of Japan, JP, Jan. 1, 2007, pp. 40-41, vol. 36, No. 1, XP009110935, ISSN: 0366-7022, DOI: 10.1246/C1. 2007.40 [retrieved on Dec. 2, 2006].

Supplementary European Search Report mailed Dec. 2, 2011 in corresponding European Patent Application No. 07707418.5.

* cited by examiner

PROCESS FOR PRODUCTION OF LASOFOXIFENE OR ANALOGUE THEREOF

TECHNICAL FIELD

The present invention relates to a process for producing lasofoxifene, known as a selective estrogen receptor modulator, or analogues thereof, a novel and useful intermediate, used for the production process, and a process for producing the same.

BACKGROUND ART

Selective estrogen receptor modulators (SERMs) generally refer to agents that exert or do not exert an estrogen effect depending on organs or tissues; for example, the agents have an antiestrogen effect on the uterus, mammary gland, etc., whereas they exert an estrogen effect on postmenopausal osteoporosis, serum cholesterol, cardiovascular system, etc. These agents are exemplified by tamoxifen, raloxifene, lasofoxifene, etc.; among these, lasofoxifene appears promising as a prophylactic or therapeutic agent of postmenopausal osteoporosis, and clinical tests thereof have currently been progressing in a large scale. The chemical structure of the lasofoxifene, (cis-6-phenyl-5-[4-(2-pyrrolidine-1-ylethoxyphenyl]-5,6,7,8-tetrahydronaphthalen-2-ol), is shown below.

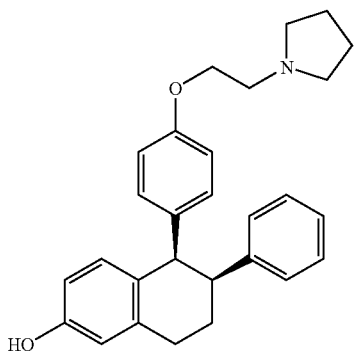

(20)

The process for producing lasofoxifene is exemplified by the following two processes. In one of the processes, a starting compound of 2-bromo-5-methoxy-toluene is brominated to obtain 1-bromo-2-bromomethyl-4-methoxy-benzene, which is then used to alkylate ethylbenzoylacetate, then to undergo decarboxylation, thereby obtaining 3-(2-bromo-5-methoxy-phenyl)-1-phenyl-propane-1-one, which is then protected by ketalation and sequentially subjected to an introduction reaction of an alkoxybenzoyl group, diketonization, formation of a naphthalene ring by McMurry coupling reaction mitigated by titanium, and an introduction reaction of an N-ethyl-pyrrolidino side chain, thereby obtaining an intermediate of cis-1-{2-[4-(6-methoxy-2-phenyl-1,2,3,4-tetrahydronaphthalene-1-yl)phenoxy]-ethyl}-pyrrolidine, followed by demethylation of a methoxy group on the tetrahydronaphthalene ring to obtain lasofoxifene (see Patent Document 1).

In the other process, a starting material of 1,4-dibromobenzene is reacted with 1-hydroxyethyl-pyrrolidine to obtain 1-[2-(4-bromophenoxy)ethyl]pyrrolidine, which is made into an organic cerium reagent then reacted with 6-methoxy-tetralone to obtain 1-{2-[4-(6-emthoxy-3,4-dihydronaphthalene-1-yl)phenoxy]ethyl}pyrrolidine. Afterwards, lasofoxifene is prepared through introduction of a bromo group into 2-position of a dihydronaphthalene ring, substitution of a bromo group with a phenyl group, hydrogenation reaction, and demethylation reaction of a methoxy group (see Patent Document 2).

However, the former process includes as many as 8 reaction steps from the starting compound to the lasofoxifene, and is thus far from an effective process.

In addition, the latter process includes a lower number of 6 reaction steps; however, in order to provide a drug substance of pharmaceutical grade, there is a disadvantage in that a coupling reaction should be carried out in the final synthesis stage with low yield using a heavy metal catalyst difficult to remove therefrom.

Furthermore, both of the processes are specialized for the production of lasofoxifene such that intermediate products in the production processes are inadequate for an intermediate for producing various lasofoxifene analogues.

Patent Document 1: Japanese Unexamined Patent Application, First Publication No. 2000-327670

Patent Document 2: Japanese Unexamined Patent Application, First Publication No. H10-503215

DISCLOSURE OF THE INVENTION

Problems to be Solved by the Invention

It is an object of the present invention to solve the problems of the prior art described above, and more specifically, to provide an effective process for producing lasofoxifene or an analogue thereof, which is superior in practical use by a reduced number of reaction steps, and also to provide a novel and useful intermediate that allows to effectively produce various lasofoxifene analogues.

Means for Solving the Problems

As a result of thorough investigation by present inventors, it has been discovered that lasofoxifene or analogues thereof can be effectively produced in a reduced number of steps and intermediate products in the production steps allow for effective production of various species of lasofoxifene analogues, and also are superior in practical utility thereof by use of a compound, represented by the formula (4) below, as an intermediate prepared under one step of three-component coupling using a compound represented by the formula (1) below, a compound represented by the formula (2) below, and a compound represented by the formula (3) below as raw compounds thereof, thereby achieving the present invention.

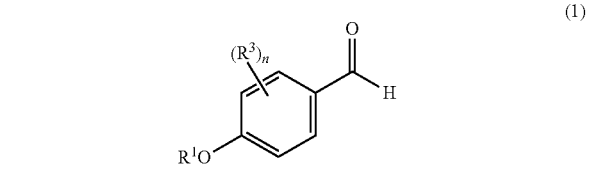

(1)

In the above formula, $R^1$ represents a hydrogen atom, an alkyl group, an acyl group, an alicyclic group, or an aromatic group; $R^3$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; and n represents an integer of 1 to 4.

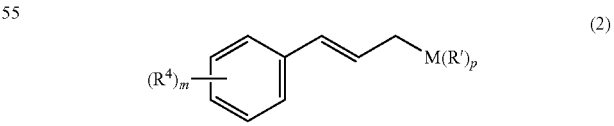

(2)

In the above formula, R' represents at least one substituent selected from a hydrogen atom, an alkyl group, an acyl group, an alicyclic group, an aromatic group, a halogen atom, a hydroxyl group, an alkyloxy group, an acyloxy group, and a cyano group; M represents a silicon atom, a boron atom, a tin atom, a zinc atom, or a magnesium atom; $R^4$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; m represents an integer of 1 to 5; and p represents an integer of 1 to 4.

(3)

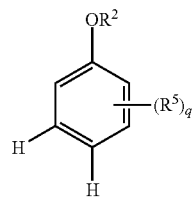

In the above formula, $R^2$ represents a hydrogen atom, an alkyl group, an acyl group, an alicyclic group, or an aromatic group; $R^5$ represents at least one substituent selected from a hydrogen atom, an alkyl group, an acyl group, an alicyclic group, an aromatic group, a halogen atom, a hydroxyl group, an alkyloxy group, and an acyloxy group; and q represents an integer of 1 to 3.

(4)

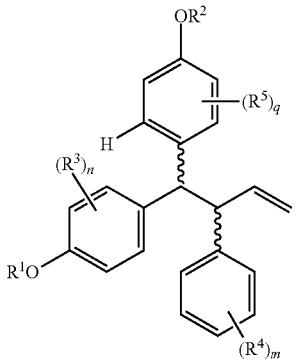

In the above formula, $R^1$ to $R^5$, n, m, and q are each the same as those described above; and the wave lines represent a bond of R or S configuration.

That is, the present invention is as follows.

According to a first aspect, in a method for producing lasofoxifene, nafoxidine, or an analogue thereof, the below sequential steps are performed:

(a) reacting compounds expressed by the formulae (1), (2) and (3) below in the presence of an acid catalyst to prepare one of a compound expressed by the formula (4) and a mixture of isomers thereof;

(1)

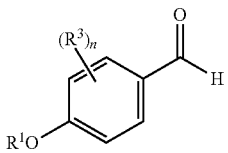

where, in the formula above, $R^1$ represents a hydrogen atom, an alkyl group, an acyl group, an alicyclic group, or an aromatic group; $R^3$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; and n represents an integer of 1 to 4;

(2)

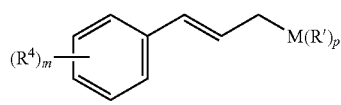

where, in the formula above, R' represents at least one substituent selected from a hydrogen atom, an alkyl group, an acyl group, an alicyclic group, an aromatic group, a halogen atom, a hydroxyl group, an alkyloxy group, an acyloxy group, and a cyano group; M represents a silicon atom, a boron atom, a tin atom, a zinc atom, or a magnesium atom; $R^4$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; m represents an integer of 1 to 5; and p represents an integer of 1 to 4;

(3)

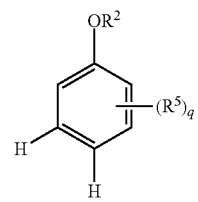

where, in the above formula, $R^2$ represents a hydrogen atom, an alkyl group, an acyl group, an alicyclic group, or an aromatic group; $R^5$ represents at least one substituent selected from a hydrogen atom, an alkyl group, an acyl group, an alicyclic group, an aromatic group, a halogen atom, a hydroxyl group, an alkyloxy group, and an acyloxy group; q represents an integer of 1 to 3;

(4)

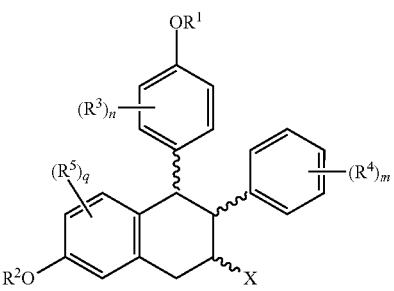

where, in the formula above, $R^1$ to $R^5$, n, m, and q are each the same as those described above; and the wave lines represent a bond of R or S configuration;

(b) obtaining a compound expressed by the formula (5) below by a halogen-induced carbocyclization reaction of one of a compound expressed by the formula (4) and a mixture of isomers thereof;

(5)

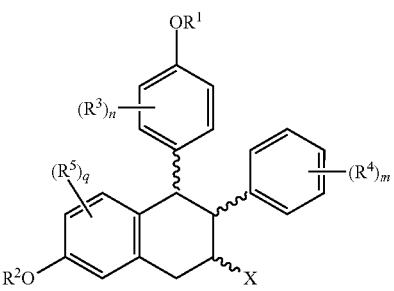

where, in the formula above, $R^1$ to $R^5$, n, m, and q are each the same as those described above; X represents a halogen atom; and the wave lines represent a bond of R or S configuration;

(c) preparing a compound expressed by the formula (8) below by de-hydrogen halide, rearrangement of a double bond, and elimination reaction of R¹ group of one of a compound expressed by the formula (5) and a mixture of isomers thereof in the presence of an alcoholate and/or an amine salt;

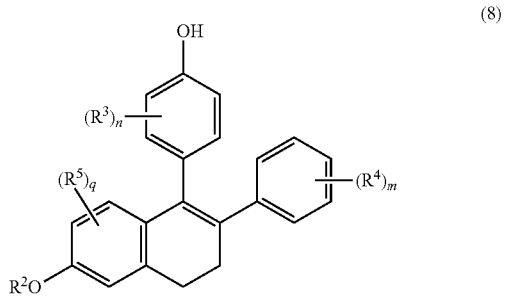

where, in the formula above, R² to R⁵, n, m, and q are each the same as those described above;

(d) obtaining one of nafoxidine and an analogue thereof by 1-pyrrolidino-ethylation of the compound expressed by the formula (8) to prepare, or performing hydrogen addition of the compound expressed by the formula (8) followed by 1-pyrrolidino-ethylation or 1-pyrrolidino-ethylation of the compound expressed by the formula (8) followed by hydrogen addition and subsequent removal of R² group to prepare one of lasofoxifene and an analogue thereof.

According to a second aspect, in a method for producing a compound expressed by the formula (5), the below sequential steps are performed of:

(a) reacting compounds expressed by the formulae (1), (2) and (3) below in the presence of an acid catalyst to prepare one of a compound expressed by the formula (4) and a mixture of isomers thereof;

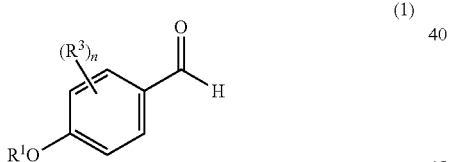

where, in the formula above, R¹ represents a hydrogen atom, an alkyl group, an acyl group, an alicyclic group, and an aromatic group; R³ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; and n represents an integer of 1 to 4;

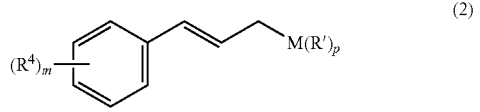

where, in the formula above, R' represents at least one substituent selected from a hydrogen atom, an alkyl group, an acyl group, an alicyclic group, an aromatic group, a halogen atom, a hydroxyl group, an alkyloxy group, an acyloxy group, and a cyano group; M represents a silicon atom, a boron atom, a tin atom, a zinc atom, or a magnesium atom; R⁴ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; m represents an integer of 1 to 5; and p represents an integer of 1 to 4;

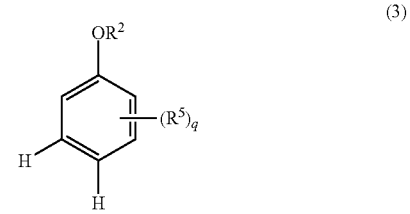

where, in the formula above, R² represents a hydrogen atom, an alkyl group, an acyl group, an alicyclic group, or an aromatic group; R⁵ represents at least one substituent selected from a hydrogen atom, an alkyl group, an acyl group, an alicyclic group, an aromatic group, a halogen atom, a hydroxyl group, an alkyloxy group, and an acyloxy group; q represents an integer of 1 to 3;

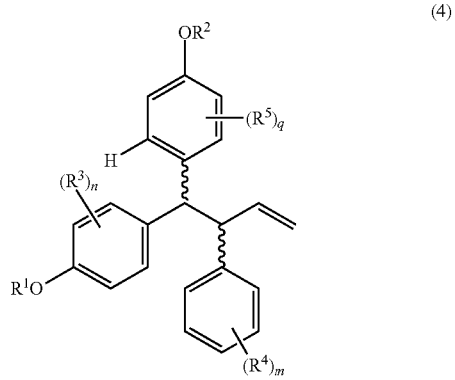

where, in the formula above, R¹ to R⁵, n, m, and q are each the same as those described above; and the wave lines represent a bond of R or S configuration;

(b) obtaining one of a compound expressed by the formula (5) below and a mixture of isomers thereof by halogen-induced carbocyclization reaction of one of a compound expressed by the formula (4) and a mixture of isomers thereof;

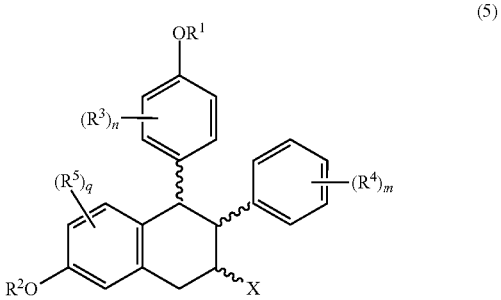

where, in the formula above, R¹ to R⁵, n, m, and q are each the same as those described above; X represents a halogen atom; and the wave lines represent a bond of R or S configuration.

In a third aspect, a method for producing a compound expressed by the formula (8) includes affecting one of a compound expressed by the formula (5) and a mixture of isomers thereof with an alcoholate and/or an amine salt to cause de-hydrogen halide, rearrangement of a double bond, and elimination reaction of $R^1$ group to prepare a compound expressed by the formula (8) below;

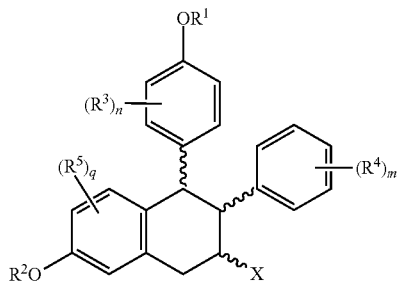

(5)

where, in the formula above, $R^1$ to $R^5$, n, m, and q are each the same as those described above; X represents a halogen atom; and the wave lines represent a bond of R or S configuration;

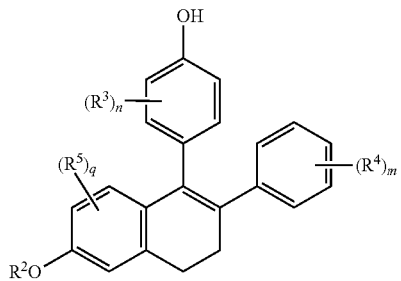

(8)

where, in the formula above, $R^2$ to $R^5$, n, m, and q are each the same as those described above.

According to a fourth aspect, in a method for producing one of nafoxidine and an analogue thereof, 1-pyrrolidino-ethylation is performed on a compound expressed by the formula (8);

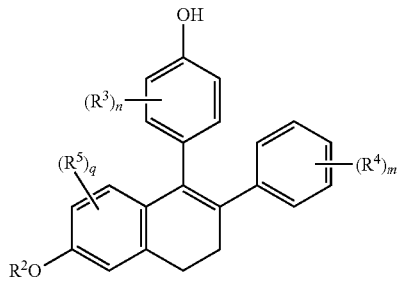

(8)

where, in the formula above, $R^2$ to $R^5$, n, m, and q are each the same as those described above.

According to a fifth aspect, in a method for producing one of lasofoxifene and an analogue thereof, hydrogen addition is performed on the compound expressed by the formula (8) below, followed by one of 1-pyrrolidino-ethylation and 1-pyrrolidino-ethylation thereof, followed by hydrogen addition and subsequent removal of $R^2$ group;

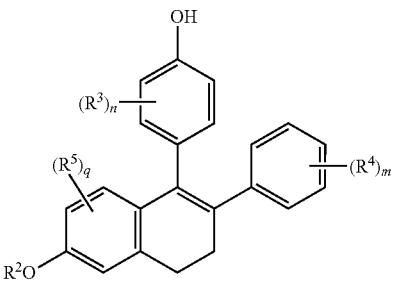

(8)

where, in the formula above, $R^2$ to $R^5$, n, m, and q are each the same as those described above.

In a sixth aspect, a compound is expressed by one of the formula (5) below and a mixture of isomers thereof;

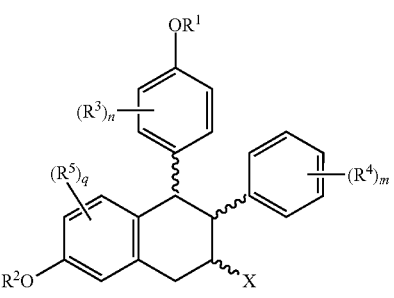

(5)

where, in the formula above, $R^1$ to $R^5$, n, m, and q are each the same as those described above; X represents a halogen atom; and the wave lines represent a bond of R or S configuration.

In a seventh aspect, a compound is expressed by the formula (8) below;

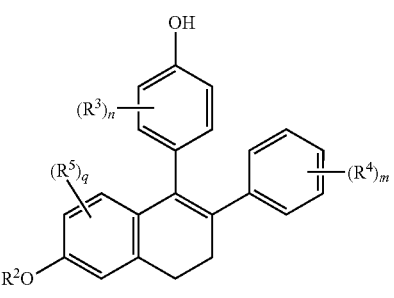

(8)

where, in the formula above, $R^2$ to $R^5$, n, m, and q are each the same as those described above.

Effects of the Invention

The present invention is characterized in that a compound, represented by the formula (4) below, which is prepared under one step of three-component coupling using a compound represented by the formula (1) below, a compound represented by the formula (2) below, and a compound represented by the formula (3) below as raw compounds thereof, is used as an intermediate of lasofoxifene and analogues thereof, whereby the process can produce lasofoxifene and analogues thereof in a reduced number of steps and is practically superior. Accordingly, the present invention can economically mass produce lasofoxifene and analogues thereof as a selective estrogen receptor modulator (SERM), particularly ones expected as a therapeutic agent of postmenopausal osteoporosis.

PREFERRED MODE FOR CARRYING OUT THE INVENTION

The structure of lasofoxifene is shown by the formula (20) below.

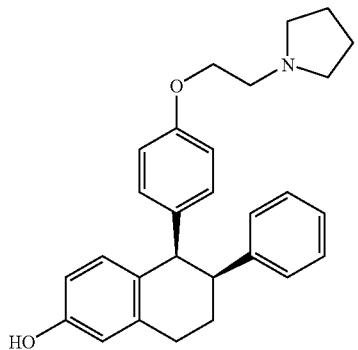

(20)

The respective steps of the production process of the present invention are explained below with reference to FIG. 1.

Production Process (FIG. 1)

Step of Three-Component Coupling

In the present invention, initially, a compound represented by the formula (4) is synthesized in one step using a compound represented by the formula (1), a compound represented by the formula (2), and a compound represented by the formula (3) as raw compounds thereof.

Preferable compounds expressed by the formula (1) are exemplified by 4-acetoxybenzaldehyde, 4-pivaloyloxybenzaldehyde, 4-propanoyloxybenzaldehyde, 4-ethoxycarbonyloxybenzaldehyde, 4-benzyloxycarbonyloxybenzaldehyde, 4-silyloxybenzaldehyde, etc. Preferable compounds expressed by the formula (2) are exemplified by trimethyl cinnamylsilane, tributyl cinnamyltin, dimethyl cinnamylboron, etc.

Compounds of the formula (3) are preferably 2-methoxybenzene, 2-ethoxybenzene, 2-benzyloxybenzene, etc.

An acid catalyst such as Lewis acids, e.g. $HfCl_4$ or proton acids, and a co-catalyst such as trimethylsilyl trifluoromethanesulfonate (TMSOTf) are used in this reaction step. As for the catalyst, trimethylsilyl chloride can be used in addition to the TMSOTf; and for the Lewis acid, metal salts of the 4th group such as $Hf(OTf)_4$, $TiCl_4$ and $TiCl_2(OTf)_2$, metal salts of 3rd group such $AlCl_3$, $BCl_3$ and $Sc(OTf)_3$, and metal salts of 2nd group such $SnCl_2$ and $Sn(OTf)_2$ can be used in addition to ones described above. Hydrochloric acid, sulfuric acid, nitric acid, hydrobromic acid, trifluoroacetic acid, trifluoromethanesulfonic acid, etc. can be used as the proton acid. These may be used alone or in combinations of two or more. Reaction temperature is in the range of 0° C. to 40° C., and may be room temperature. The reaction time is in the range of 1 to 10 hours.

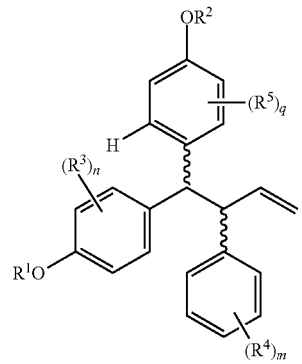

(4)

Here, in the formula above, $R^1$ to $R^5$, n, m, and q are each the same as those described above; and the wave lines represent a bond of R or S configuration.

Step of Cyclization Reaction

The mixture of isomers, obtained in the abovementioned step, is then subjected to a halogen-induced carbocyclization reaction using a halogenating agent such as imide N-chlorosuccinate, imide N-bromosuccinate, imide N-iodosuccinate and $I(Py)_2BF_4$ and an acid such as $HBF_4$, $BF_3$—$OEt_2$ and $CF_3SO_3H$ in the presence of a solvent such as ethylene ether and methylene chloride, whereby a mixture of isomers of compounds expressed by the formula (5) is prepared.

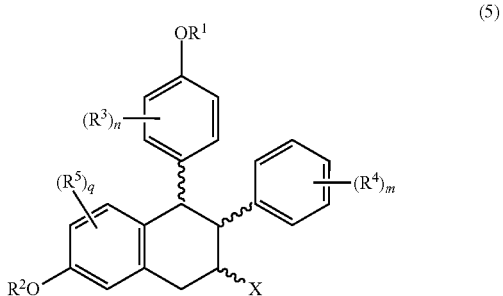

(5)

Here, in the formula above, $R^1$ to $R^5$, n, m, and q are each the same as those described above; X represents a halogen atom; and the wave lines represent a bond of R or S configuration.

The reaction temperature is in the range of −78° C. to 0° C.

The mixture of isomers is a mixture of compounds expressed by the abovementioned formula (5), more specifically, by a mixture of compounds of eight species in total containing enantiomers of respective compounds expressed by the formulae (11) to (14) below.

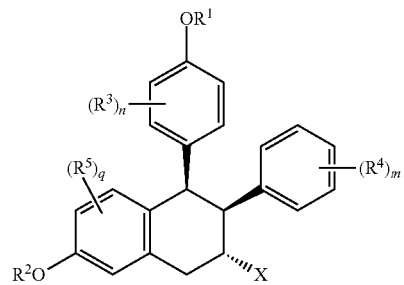

(11)

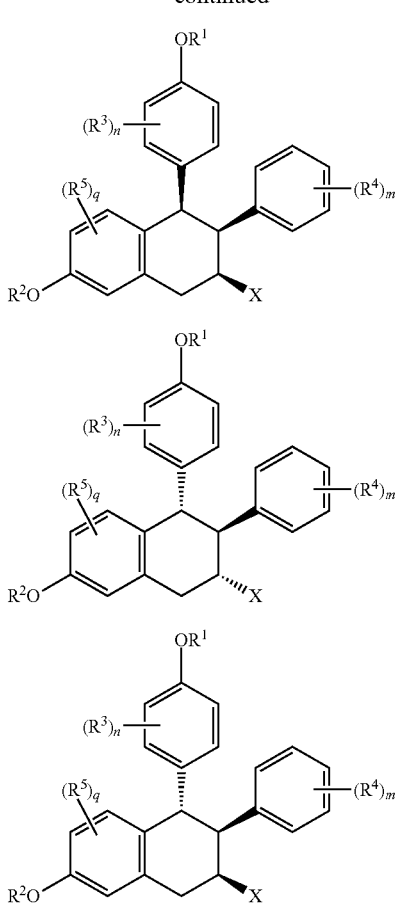

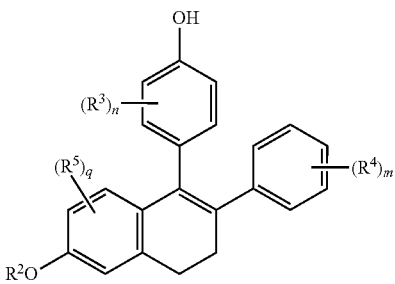

Here, $R^3$, $R^4$, $R^5$, n, m, q and wave lines are each the same as those described above.

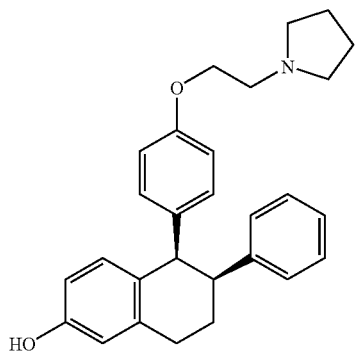

Here, $R^3$, $R^4$, $R^5$, n, m, and q are each the same as those described above.

Step of Producing Lasofoxifene and Nafoxidine

From the compound of the formula (8), lasofoxifene expressed by the formula (20) can be obtained through hydrogen addition, introduction of a side chain, and removal of an alkyl group in sequence; incidentally, the hydrogen addition may be carried out after the introduction of a side chain, and then an alkyl group may be removed. In this case, the reaction goes through nafoxidine or an analogue thereof by introducing a side chain.

Here, in the formulae (11) to (14), $R^3$, $R^4$, $R^5$, n, m, and q are each the same as those described above.

Step of Removing Acyl Group and Removing Iodine

From the mixture of isomers obtained in the abovementioned step, compounds of the formula (8) can be obtained through de-hydrogen halide, rearrangement of a double bond, and elimination reaction of $R^1$ group by action of alcoholates such as t-butylate, methylate and ethylate or alcoholates and amine bases such as DBU, DBN and DABCO, without separating or isolating the respective compounds. These reactions may be carried out sequentially or simultaneously.

When amine bases such as DBU are used in these reactions and an intermediate product containing a compound expressed by the formula (10) below is yielded, the intermediate product may not be removed particularly in this step and a plurality of the reaction steps can progress in one reaction vessel. The reaction temperature is the range of 0° C. to 80° C., and preferably the range of room temperature to 50° C.

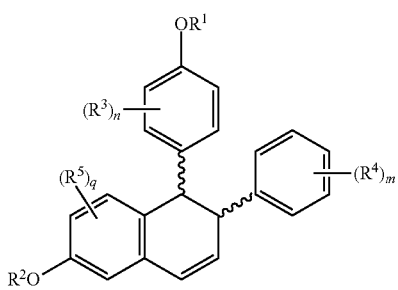

The hydrogen addition is carried out in the presence of a metal catalyst such as $Pd(OH)_2$, Pd/carbon, Pd black, Pt black and rhodium chloride complexes under normal pressure to a pressure of about 500 kPa; the introduction of a side chain is carried out by reaction with pyrrolidinoethyl bromide or pyrrolidinoethyl chloride in the presence of chlorine or with 1-(2-hydroxyethyl)pyrrolidine in the presence of an azo reagent such as diethylazodicarboxylate and diisopropyl dicarboxylate and a reducing agent such as triphenylphosphine and quinones. The removal of an alkyl group is carried out by action of a strong acid such as $BBr_3$, 47% HBr and HBr/acetic acid.

When $R^2$ is a methyl group in the formula (8), nafoxidine expressed by the formula (21) below can be obtained through introducing a side chain in a similar manner as described above. When $R^2$ is other alkyl groups, nafoxidine analogues are obtained.

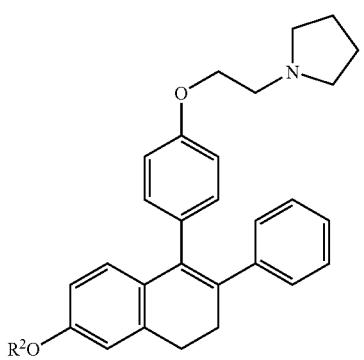

(21)

The present invention is explained with specific reference to examples hereinafter; however, the present invention should not be limited thereto. In regards to the examples below, Examples 2 to 4 relate to a reaction without separating an intermediate mixture of isomers, and Examples 5 and 6 relate to a reaction using a single compound of a mixture of isomers.

EXAMPLE 1

Construction of Triarylbutene Skeleton by Three-Component Coupling Reaction 1-(4-methoxyphenyl)-2-phenyl-1-(4-pivaloyloxyphenyl)-3-butene

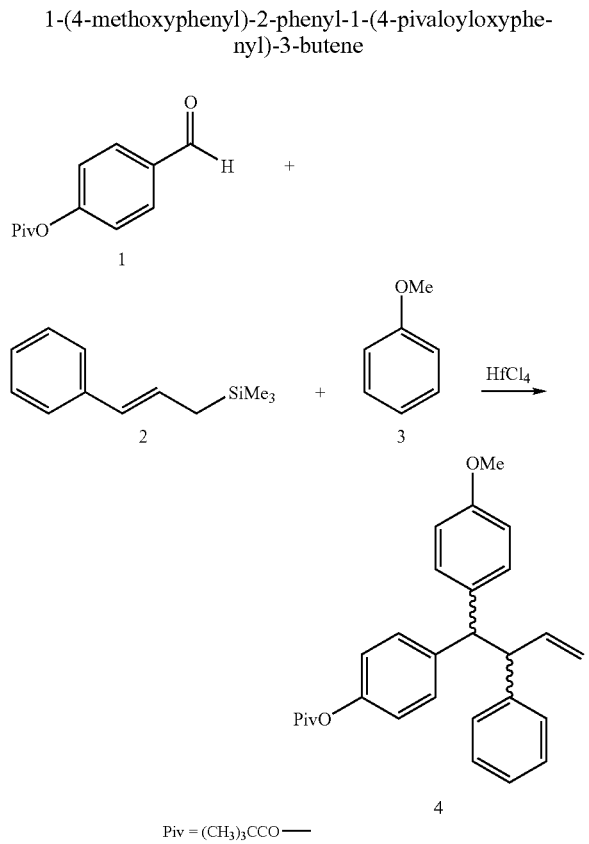

Hafnium chloride (39.2 mg, 0.122 mmol) was suspended in anisole (3, 0.02 mL) under an argon atmosphere, and then an anisole solution (0.22 mL) of 4-(pivaloyloxy)benzaldehyde (1, 25 mg, 0.121 mmol) and trimethyl cinnamylsilane (2, 46.7 mg, 0.245 mmol) was slowly added dropwise thereto under cooling by ice. The reaction mixture was stirred overnight at room temperature, then a saturated aqueous sodium bicarbonate solution (5 mL) was poured thereto, and the mixture was intensively stirred and extracted by adding diethyl ether (10 mL). The reaction mixture was further extracted two times using diethyl ether (10 mL), and then an organic layer was collected and rinsed with a saturated aqueous sodium chloride solution (5 mL), followed by drying with anhydrous magnesium sulfate and concentration thereof. The residue was purified by thin layer chromatography (hexane/methylene chloride/diethyl ether=4/1/1) to obtain the title compound as a colorless oily substance (37.7 mg, yield 75%, cin/anti mixture).

$^1$H NMR (CDCl$_3$, tetramethylsilane) δ (ppm): 1.20 and 1.26 (s, 9H), 3.59 and 3.70 (s, 3H), 4.01 (dd, 1H, J=7.8, 11.3 Hz), 4.19 (d, 1H, 11.3 Hz), 4.7-4.9 (m, 2H), 5.8-5.9 (m, 1H), 6.6-7.3 (m, 13H).

Infrared absorption spectrum (liquid membrane technique) cm$^{-1}$: 2974, 1749, 1610, 1511, 1462, 1252, 1203, 1167, 1120, 1032, 753, 700.

Mass spectrum m/e: calculated value 415.23 as (C$_{28}$H$_{30}$O$_3$+H)$^+$, experimental value 415.23

EXAMPLE 2

Construction of Tetrahydronaphthalene Skeleton by Cyclization Reaction

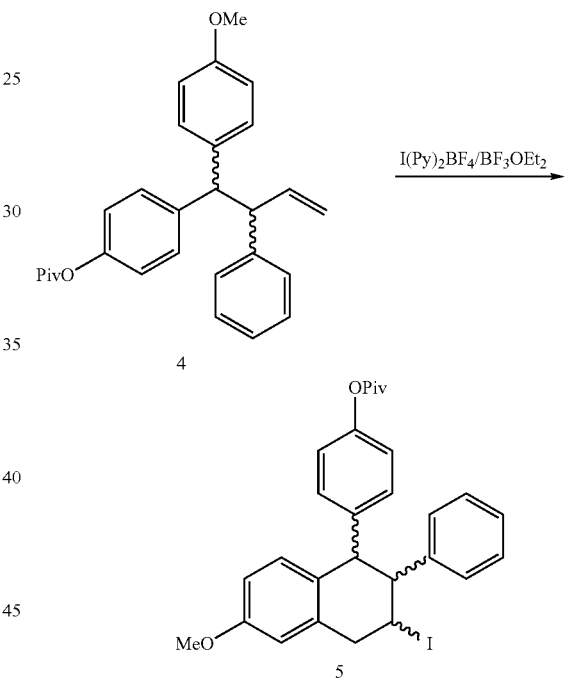

Bis(pyridine)iodonium tetrafluoroborate (65.8 mg, 0.177 mmol) was suspended in methylene chloride (3.4 mL), and the suspension was cooled to −78° C. in a dry ice/acetone bath. A methylene chloride (1.8 mL) solution of 1-(4-methoxyphenyl)-2-phenyl-1-(4-pivaloyloxyphenyl)-3-butene (4, 56.0 mg, 0.135 mmol) was added to the suspension, and also a tribromoborane diethyl ether complex (0.015 mL, 0.118 mmol) was added stepwise three times. Thereafter, the reactant was stirred at −78° C. for 1 hour, then a saturated aqueous ammonium chloride solution (5 mL) was added thereto to stop the reaction, and the reactant was cooled to room temperature and then extracted three times with diethyl ether (10 mL). An organic layer was collected and rinsed with a saturated aqueous sodium chloride solution (10 mL), followed by drying with anhydrous sodium sulfate and concentrating. The residue was purified by thin layer chromatography to obtain the title compound as a light yellow oily substance (51.6 mg, yield 71%).

$^1$H NMR (CDCl$_3$, tetramethylsilane) δ (ppm): 1.32, 1.35 and 1.32 (s, 9H), 3.3 (m, 1H), 3.7-3.9 (m, 5H), 4.2 (d, 1H, J=10.6 Hz), 4.7-4.8 (m, 1H), 6.6-7.2 (m, 12H).

Infrared absorption spectrum (liquid membrane technique) cm$^{-1}$: 2972, 1751, 1610, 1510, 1503, 1122, 1031.

Mass spectrum m/e: calculated value 541.12 as (C$_{28}$H$_{29}$IO$_3$+H)$^+$, experimental value 541.12

EXAMPLE 3

Construction of Dihydronaphthalene Skeleton by De-Hydrogen Halide Reaction 7-methoxy-3-phenyl-4-(4-pivaloyloxyphenyl)-3,4-dihydronaphthalene (6)

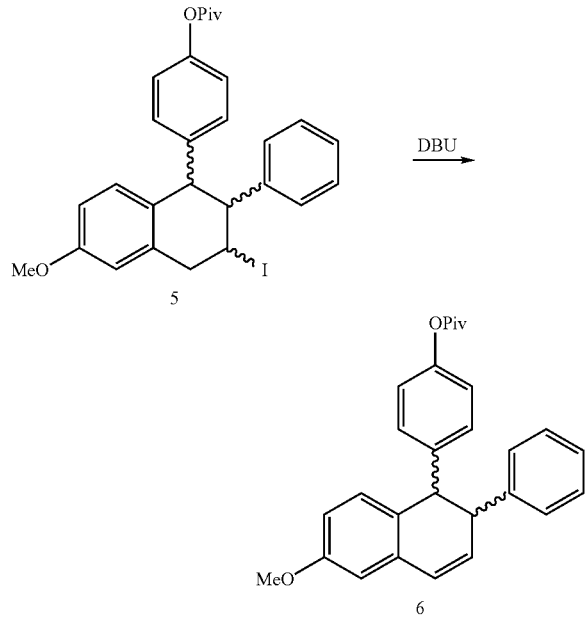

DBU = 1,8-Diazabicyclo[5.4.0]undec-7-ene

2-Iodo-7-methoxy-3-phenyl-4-(4-pivaloyloxyphenyl)-1,2,3,4-tetrahydronaphthalene (5, 39.4 mg, 0.0729 mmol) was dissolved in toluene (1.5 mL), then 1,8-diazabicyclo[5.4.0]undecene-7 (DBU, 0.035 mL, 0.234 mmol) was added thereto, and the mixture was stirred for 15 minutes while heating at 80° C. After allowing cooling, a saturated aqueous ammonium chloride solution (10 mL) was added under cooling by ice, and then the mixture was intensively stirred and extracted by adding ether (10 mL). The reaction mixture was further extracted two times using ether (10 mL), and then an organic layer was collected and rinsed with a saturated aqueous sodium chloride solution, followed by drying with anhydrous magnesium sulfate and concentration thereof. The residue was purified by thin layer chromatography (benzene/hexane=10/1) to obtain the title compound (6, 22.7 mg) as a colorless oily substance (yield 75%).

$^1$H NMR (CDCl$_3$, tetramethylsilane) δ (ppm): 1.34 and 1.36 (s, 9H), 3.76 and 3.80 (s, 3H), 3.84 (dd, 1H, J=4.2, 7.5 Hz), 4.17 (d, 1H, J=7.5 Hz), 5.98 (dd, 1H, 4.2, 9.6 Hz), 6.6-7.2 (m, 12H).

EXAMPLE 4

4-(4-hydroxyphenyl)-7-methoxy-3-phenyl-1,2-dihydronaphthalene (7)

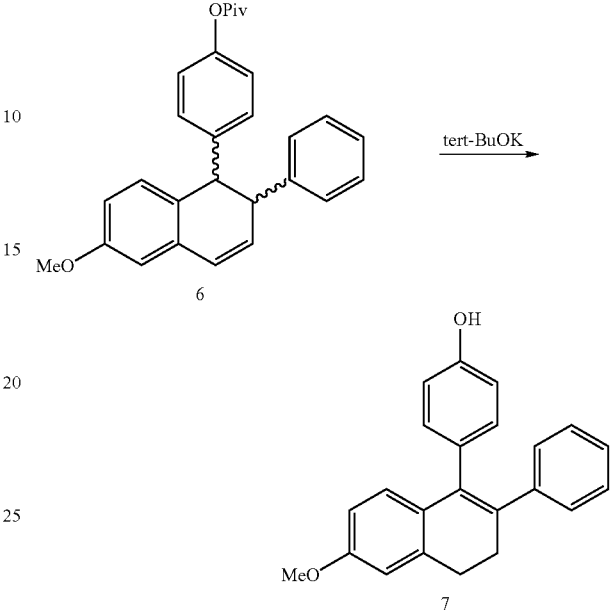

Rearrangement Reaction of Double Bond

A solution of 7-methoxy-3-phenyl-4-(4-pivaloyloxyphenyl)-3,4-dihydronaphthalene (6, 29.3 mg, 0.0710 mmol) in dimethyl sulfoxide (0.8 mL) was added to a solution of tertiary butoxy potassium (40.3 mg, 0.359 mmol) in dimethyl sulfoxide (0.6 mL), and the reaction mixture was stirred at room temperature for one day. A saturated aqueous ammonium chloride solution (10 mL) was added to the reaction mixture, which was sufficiently stirred and then extracted three times by diethyl ether (10 mL). An organic layer was collected and rinsed with a saturated aqueous sodium chloride solution (10 mL), followed by drying with anhydrous magnesium sulfate and concentration thereof. The residue was purified by thin layer chromatography (toluene/ethyl acetate=10/1) to obtain the title compound (7, 16.0 mg, yield 69%).

$^1$H NMR (CDCl$_3$, tetramethylsilane) δ (ppm) 2.91 (ddd, 2H), 2.75 (ddd, 2H), 3.79 (s, 3H), 6.6-7.2 (m, 12H).

EXAMPLE 5

Construction of Tetrahydronaphthalene Skeleton by Cyclization Reaction

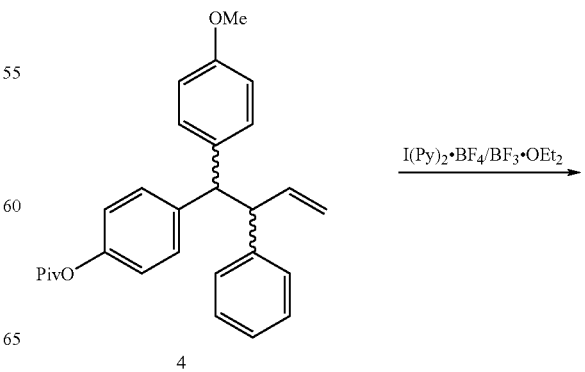

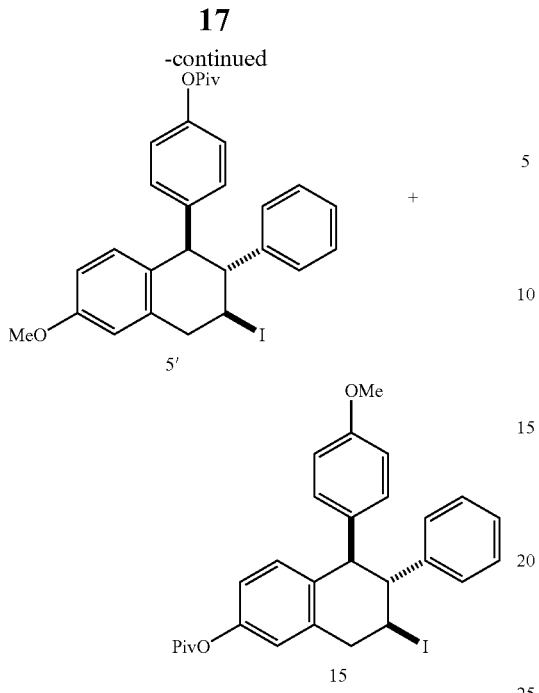

Bis(pyridine)iodonium tetrafluoroborate (57.1 mg, 0.154 mmol) was suspended in methylene chloride (3.4 mL), and the suspension was cooled to −78° C. in a dry ice/acetone bath. A methylene chloride (2 mL) solution of 1-(4-methoxyphenyl)-2-phenyl-1-(4-pivaloyloxyphenyl)-3-butene (4, 56.0 mg, 0.135 mmol) was added to the suspension, and also a tribromoborane diethyl ether complex (0.015 mL, 0.118 mmol) was added stepwise three times. The reactant was stirred at −78° C. for 2 hours, and then a saturated aqueous ammonium chloride solution was added thereto to stop the reaction. Diethyl ether was added to the mixture, which was then extracted three times, and then an organic layer was collected and rinsed with a saturated aqueous sodium chloride solution, followed by drying with anhydrous magnesium sulfate and concentration thereof. The residue was purified by thin layer chromatography (toluene) to obtain two compounds: a compound having a lower Rf value in the thin layer chromatography was a compound 5' (29.9 mg, yield 41%) suited to a precursor of lasofoxifene or nafoxidine and another compound having a larger Rf value was a compound 15 (20.0 mg, yield 27%, cyclization yield 68%).

2-iodo-7-methoxy-3-phenyl-4-(4-pivaloyloxyphenyl)-1,2,3,4-tetrahydronaphthalene (5'), amorphous solid $^1$H NMR (CDCl$_3$, tetramethylsilane) δ (ppm):7.2-6.5 (m, 12H, Ph), 4.68 (dt, 1H, J=5.1, 11.7 Hz, 2-H), 4.13 (d, 1H, J=10.5 Hz, 4-H), 3.76 (dd, 1H, J=11.7, 16.2 Hz, 1-Htrans), 3.67 (s, 3H, OCH$_3$), 3.65 (dd, 1H, J=5.1, 16.2 Hz, 1-Hcis), 3.21 (dd, 1H, J=10.5, 11.7 Hz, 3-H), m, 1H), 1.23 (s, 9H, C(CH$_3$)$_3$).

Infrared absorption spectrum (KBr) cm$^{-1}$: 2971, 1750, 1610, 1503, 1271, 1119, 1032.

Mass spectrum m/e: calculated value 563.11 as (C$_{28}$H$_{29}$IO$_3$+Na)$^+$, experimental value 563.11.

2-iodo-4-(4-methoxyphenyl)-3-phenyl-7-pivaloyloxy-1,2,3,4-tetrahydronaphthalene (15), Colorless Oil $^1$H NMR (CDCl$_3$, tetramethylsilane) δ (ppm): 7.3-6.6 (m, 1H, Ph), 4.77 (ddd, 1H, J=5.1, 11.7, 12.0 Hz, 2-H), 4.19 (d, 1H, J=10.2 Hz, 4-H), 3.87 (dd, 1H, J=11.7, 15.9 Hz, 1-H trans), 3.75 (dd, 1H, J=5.1, 15.9 Hz, 1-Hcis), 3.72 (s, 3H, OCH$_3$), 3.32 (dd, 1H, J=10.2, 12.0 Hz, 3-H), 1.35 (s, 9H, C(CH$_3$)$_3$). Infrared absorption spectrum (liquid membrane technique) cm$^{-1}$: 2972, 1750, 1603, 1571, 1504, 1266, 1202, 1119, 1032.

Mass spectrum m/e: calculated value 563.11 as (C$_{28}$H$_{29}$IO$_3$+Na)$^+$, experimental value 563.11.

EXAMPLE 6

Example of Simultaneous Occurrence of Double-Bond Forming Reaction by De-Hydrogen Halide and Rearrangement of Resulting Double Bond 4-(4-hydroxyphenyl)-7-methoxy-3-phenyl-1,2-dihydronaphthalene (common intermediate: 7 of nafoxidine and lasofoxifene)

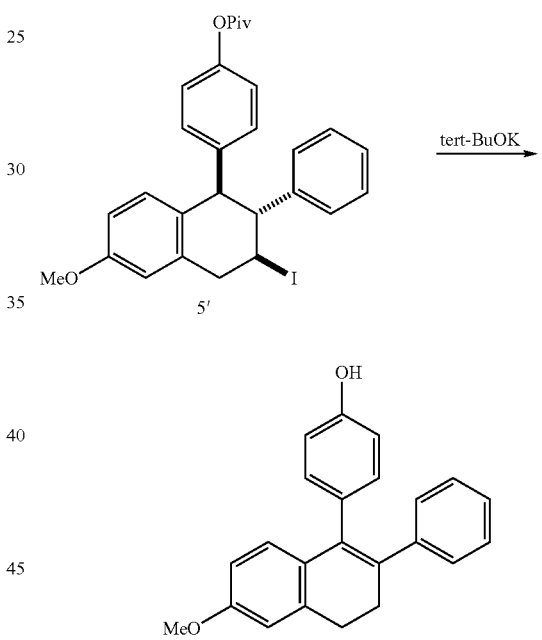

Potassium tert-butoxide solution 0.5 mol/L in dimethyl sulfoxide (1.10 mL, 0.55 mmol) was added to and dissolved in 2-iodo-7-methoxy-3-phenyl-4-(4-pivaloyloxyphenyl)-1,2,3,4-tetrahydronaphthalene (5', 74.4 mg, 0.138 mmol) under an argon atmosphere, and the resulting aubergine solution was stirred for 1 hour while heating at 90° C. Thereafter, the reaction mixture was cooled with ice, and then a saturated aqueous ammonium chloride solution (7 mL) was added thereto and sufficiently stirred, followed by extracting four times with a mixed liquid (4 mL) of hexane/diethyl ether (1:1). An organic layer was collected, followed by drying with anhydrous magnesium sulfate and concentration thereof. The residue was purified by silica gel column chromatography (hexane/ethyl acetate=4/1) to obtain the title compound (7, 41.1 mg, yield 89%), the same as that of Example 4.

The dimethyl sulfoxide was sufficiently degassed prior to use thereof.

EXAMPLE 7

7-methoxy-3-phenyl-4-[4-(2-pyrrolidine-1-ylethoxy)]phenyl-1,2-dihydronaphthalene (nafoxidine: 21)

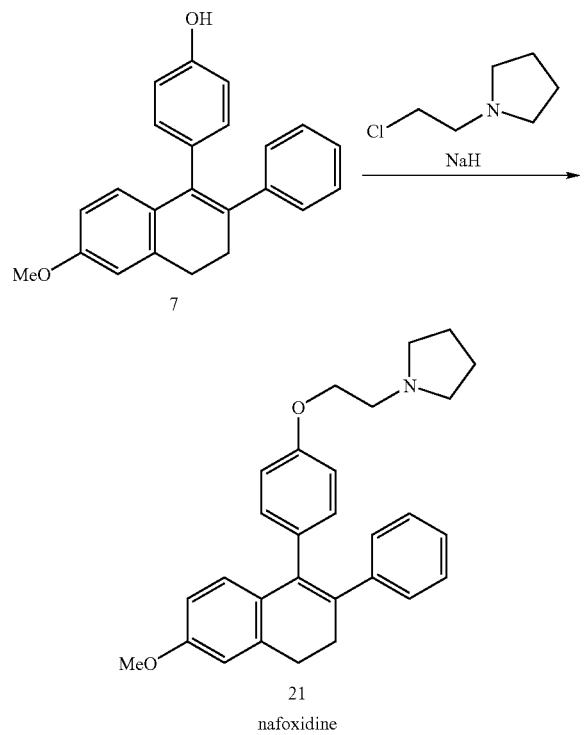

4-(4-Hydroxyphenyl)-7-methoxy-3-phenyl-1,2-dihydronaphthalene (7, 31.7 mg, 0.0965 mmol) was dissolved in N,N-dimethylformamide (1 mL) under an argon atmosphere, and then 60% sodium hydride (13.4 mg, 0.335 mmol) was added thereto and stirred for 20 minutes at room temperature.

Pyrrolidinoethyl chloride hydrochloride (33.4 mg, 0.196 mmol) was added to the mixture and stirred at 50° C. for 11 hours. Thereafter, the reaction mixture was cooled with ice, and then a saturated aqueous ammonium chloride solution was poured thereto to stop the reaction, followed by extracting four times with ethyl acetate. An organic layer was collected, dried with anhydrous sodium sulfate and concentrated, and then the residue was purified by thin layer chromatography (hexane/ethyl acetate/concentrated ammonia water=7/3/1) to obtain the title compound (21: nafoxidine, 3.5 mg, yield 82%) as a light yellow oily substance.

$^1$H NMR (CDCl$_3$, tetramethylsilane) δ (ppm): 7.2-6.5 (m, 12H, Ph), 4.18 (t, 2H, J=3.6 Hz, OCH$_2$), 3.80 (s, 3H, OCH$_3$), 3.04 (t, 2H, J=3.6 Hz, NCH$_2$), 2.94 (m, 2H, 1-H), 2.84 (m, 4H, pyrrolidine 2-H), 2.77 (m, 2H, 2-H), 1.90 (m, 4H, pyrrolidine 3-H).

Infrared absorption spectrum (liquid membrane technique) cm$^{-1}$: 3031, 2936, 1669, 1606, 1568, 1508, 1241, 1174, 1037.

Mass spectrum m/e: calculated value 426.24 as (C$_{29}$H$_{31}$NO$_2$+H)$^+$, experimental value 426.24

EXAMPLE 8

7-methoxy-3-phenyl-4-[4-(2-(pyrrolidine-1-yl)ethoxy)]phenyl-1,2,3,4-tetrahydronaphthalene (16)

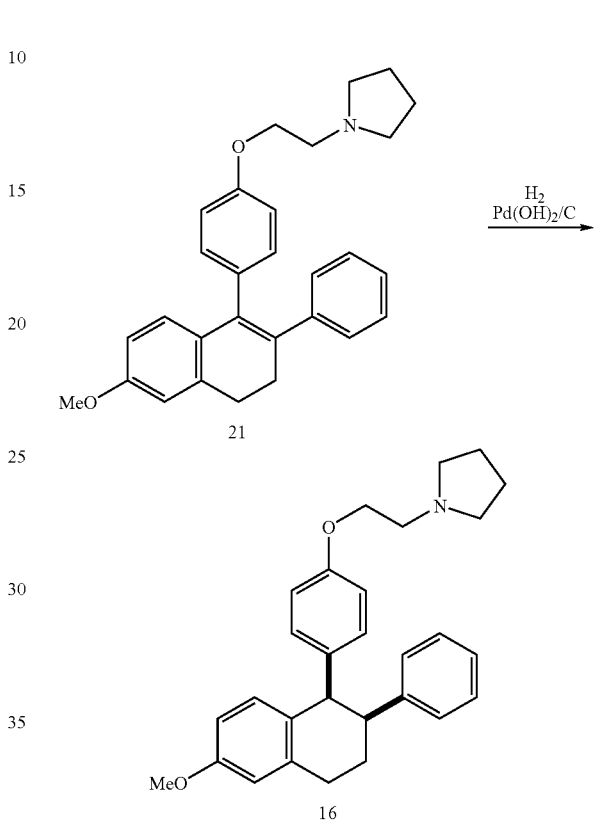

7-Methoxy-3-phenyl-4-[4-(2-(pyrrolidine-1-yl)ethoxy)]phenyl-1,2-dihydronaphthalene (21, 36.0 mg, 0.0846 mmol) was dissolved in ethanol (3 mL) in a pressure-resistant container, then palladium hydroxide-carbon (36.0 mg) was added thereto, and then the container was filled with hydrogen and sealed, followed by stirring for 22 hours at 50° C. under 0.25 MPa. Thereafter, the catalyst was passed through a Cerite layer to filter and separate, a filtered layer was rinsed with ethyl acetate, and then an organic layer was collected and concentrated to obtain the title compound (16) as a colorless oily substance (25.2 mg, yield 70%).

$^1$H NMR (CDCl$_3$, tetramethylsilane) δ (ppm):7.2-6.6 (m, 8H, Ph), 6.55 (d, 2H, J=8.7 Hz, Ph), 6.31 (d, 2H, J=8.7 Hz, Ph), 4.24 (d, 1H, J=5.1 Hz, 4-H), 4.00 (t, 2H, J=6.0 Hz, OCH$_2$), 3.82 (s, 3H, OCH$_3$), 3.36 (ddd, 1H, J=2.1, 5.1, 12.9 Hz, 3-H), 3.06 (m, 2H, 1-H), 2.85 (t, 2H, J=6.0 Hz, NCH$_2$), 2.7-2.5 (m, 4H, pyrrolidine 2-H), 2.19 (m, 1H, 2-H), 1.80 (m, 1H, 2-H), 1.7-1.8 (m, 4H, pyrrolidine 3-H).

Infrared absorption spectrum (liquid membrane technique) cm$^{-1}$: 2932, 1608, 1506, 1460, 1240, 1178, 1155, 1038, 823.

Mass spectrum m/e: calculated value 428.26 as (C$_{29}$H$_{33}$NO$_2$+H)$^+$, experimental value 428.26.

Cameron et al. describe the abovementioned hydrochloride compound in Japanese Unexamined Patent Application, First Publication No. H10-503215. The abovementioned $^1$H-NMR and the mass spectrum correlate well with those of the hydrochloride reported by Cameron et al.

EXAMPLE 9

7-hydroxy-3-phenyl-4-[4-(2-pyrrolidine-1-ylethoxy)]phenyl-1,2,3,4-tetrahydronaphthalene(20: lasofoxifene)

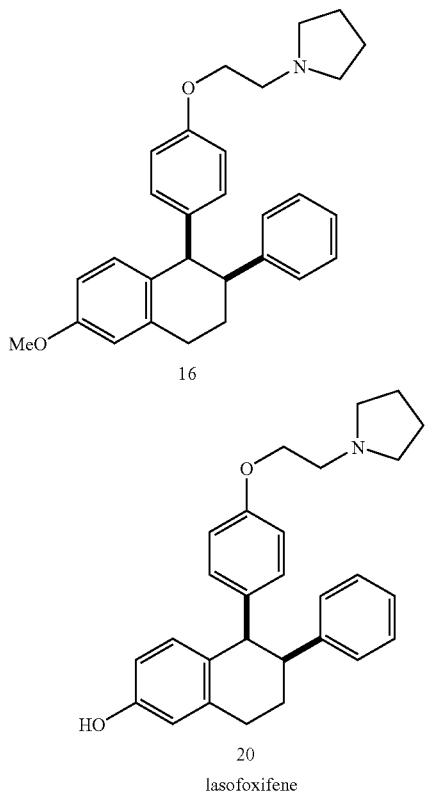

16 lasofoxifene

7-Methoxy-3-phenyl-4-[4-(2-pyrrolidine-1-ylethoxy)]phenyl-1,2,3,4-tetrahydronaphthalene (16, 10.1 mg, 0.0236 mmol) was dissolved in methylene chloride (0.6 mL), and the solution was cooled to −78° C., and then boron tribromide/methylene chloride solution 1 mol/L (120 µL, 0.12 mmol) was slowly added thereto dropwise. Thereafter, the reactant was warmed to −23° C., and allowed to further react at 0° C. for 2 hours. Thereafter, a saturated aqueous sodium hydrogen carbonate solution was added thereto to stop reaction, followed by extracting with methylene chloride. After further extracting three times with ethyl acetate, an organic layer was collected, dried with anhydrous sodium sulfate and concentrated. The residual was purified by thin layer chromatography (hexane/ethyl acetate/concentrated ammonia water=3/6/1) to obtain lasofoxifene (20) as a light yellow oily substance (7.4 mg, yield 76%).

$^1$H NMR (CDCl$_3$, tetramethylsilane) δ (ppm): 7.1-6.4 (m, 8H, Ph), 6.27 (d, 2H, J=8.7 Hz, Ph), 6.16 (d, 2H, J=8.7 Hz, Ph), 4.10 (d, 1H, J=4.8 Hz, 4-H), 3.91 (t, 2H, J=4.2 Hz, OCH$_2$), 3.24 (dd, 1H, J=4.8, 11.4 Hz, 3-H), 3.0-2.6 (m, 8H, 1-H, NCH$_2$, pyrrolidine 2-H), 2.00 (m, 1H, 2-H), 1.8 (m, 4H, pyrrolidine 3-H), 1.65 (m, 1H, 2-H).

Infrared absorption spectrum (liquid membrane technique) cm$^{-1}$: 3471, 2928, 2873, 1668, 1506, 1455, 1177, 1035, 823, 757.

Mass spectrum m/e: calculated value 414.24 as (C$_{28}$H$_{31}$NO$_2$+H)$^+$, experimental value 414.24.

The abovementioned spectrum correlates well with that of the Patent Document (Japanese Unexamined Patent Application, First Publication No. H10-503215) reported by Cameron et al.

Figure 1:
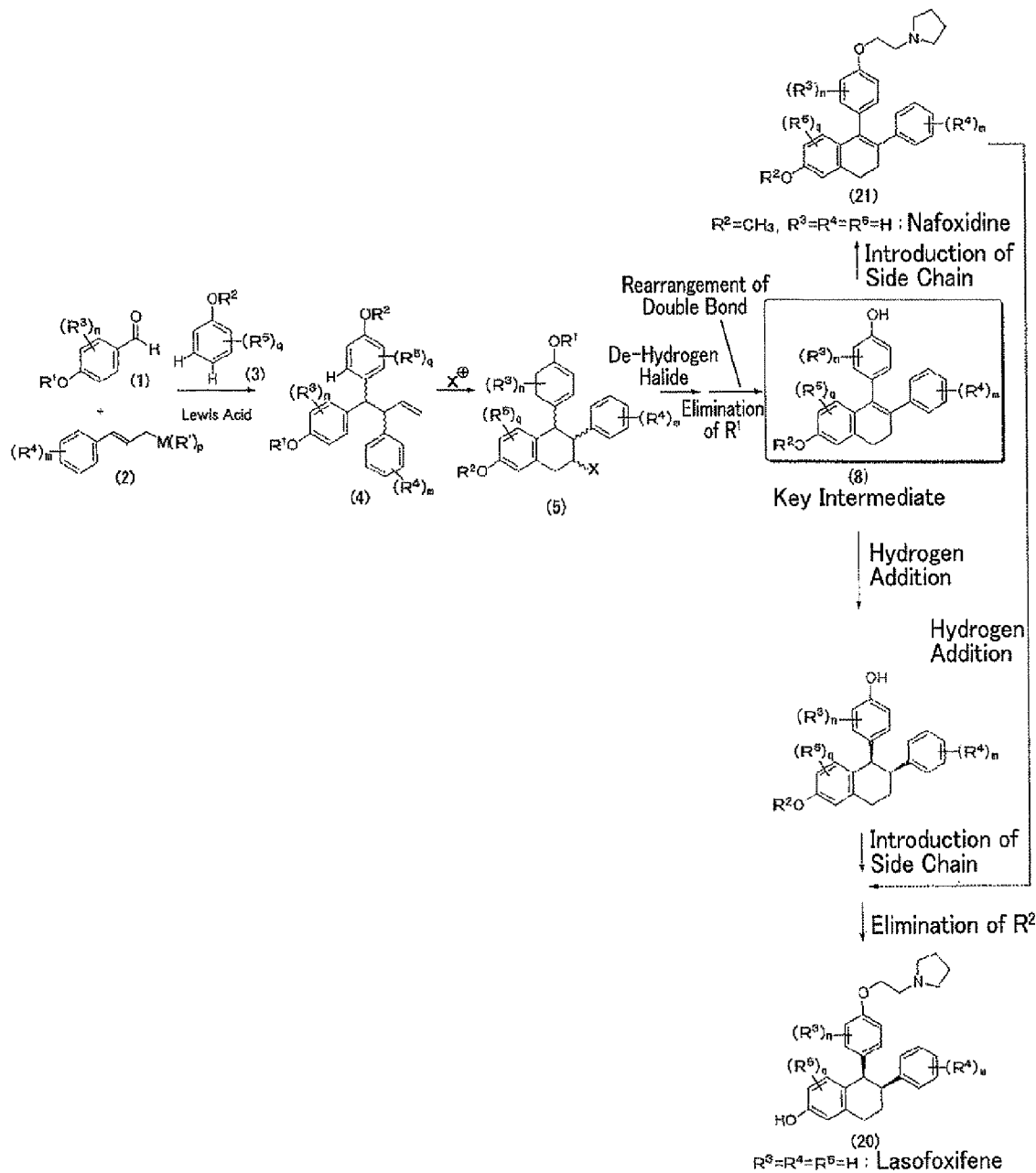
FIG. 1 schematically shows the process to produce lasofoxifene and nafoxidine according to the present invention.
Figure 2:
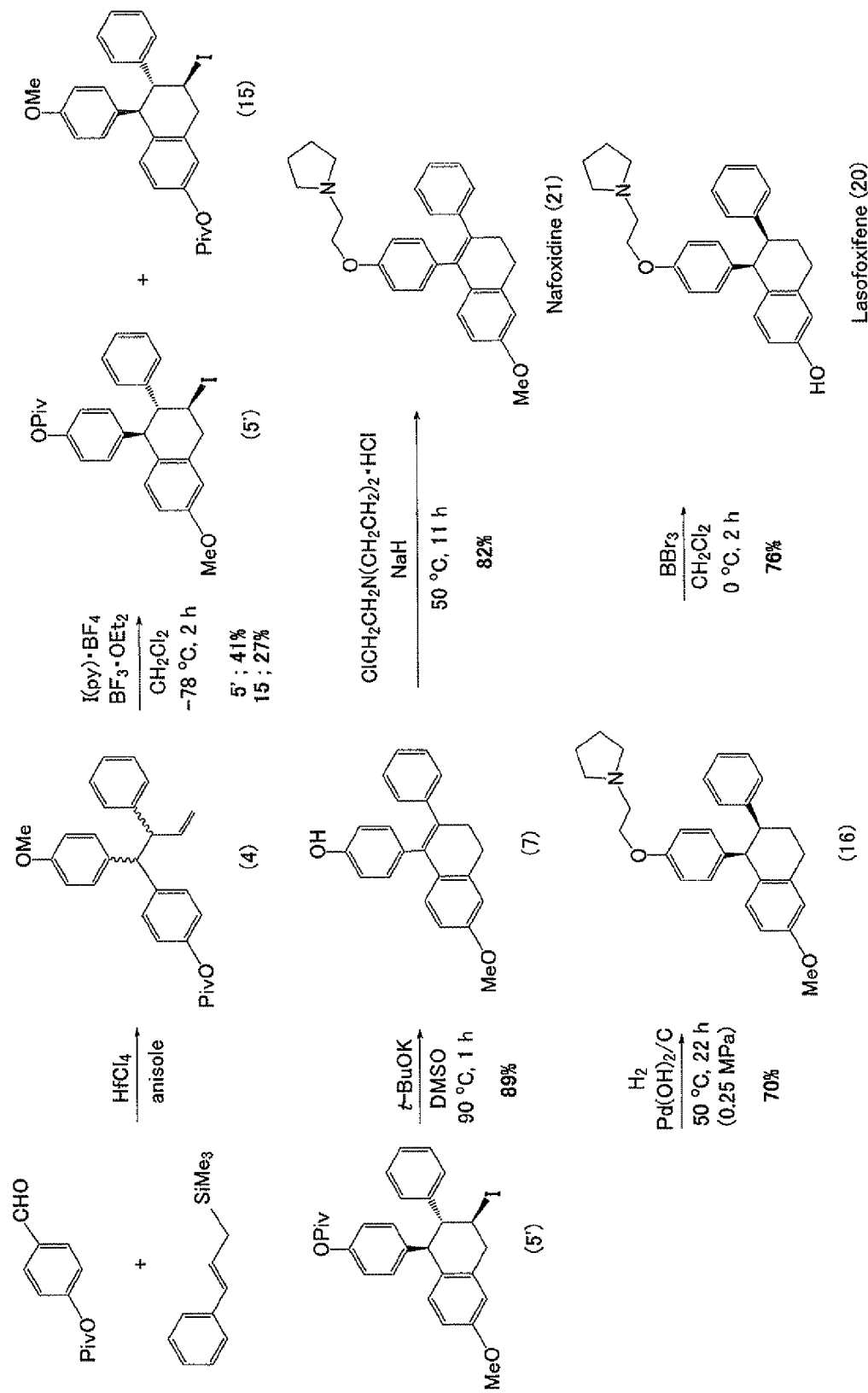
FIG. 2 schematically shows reaction steps of Examples 1 to 9 according to the present invention.

The invention claimed is:

1. A method for producing a compound expressed by the formula (5), comprising the following sequential steps of:
   (a) reacting compounds expressed by the formulae (1), (2) and (3) below in the presence of an acid catalyst to prepare one of a compound expressed by the formula (4) or a mixture of stereoisomers thereof;

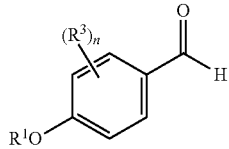

(1)

where, in the formula above, R$^1$ represents a hydrogen atom, an alkyl group, an acyl group, an alicyclic group, or an aromatic group; R$^3$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; and n represents an integer of 1 to 4;

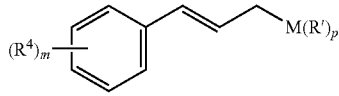

(2)

where, in the formula above, R' represents at least one substituent selected from a hydrogen atom, an alkyl group, an acyl group, an alicyclic group, an aromatic group, a halogen atom, a hydroxyl group, an alkyloxy group, an acyloxy group, and a cyano group; M represents a silicon atom, a boron atom, a tin atom, a zinc atom, or a magnesium atom; R$^4$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; m represents an integer of 1 to 5; and p represents an integer of 1 to 4;

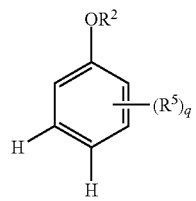

(3)

where, in the formula above, R$^2$ represents a hydrogen atom, an alkyl group, an acyl group, an alicyclic group, or an aromatic group; R$^5$ represents at least one substituent selected from a hydrogen atom, an alkyl group, an acyl group, an alicyclic group, an aromatic group, a halogen atom, a hydroxyl group, an alkyloxy group, and an acyloxy group; q represents an integer of 1 to 3;

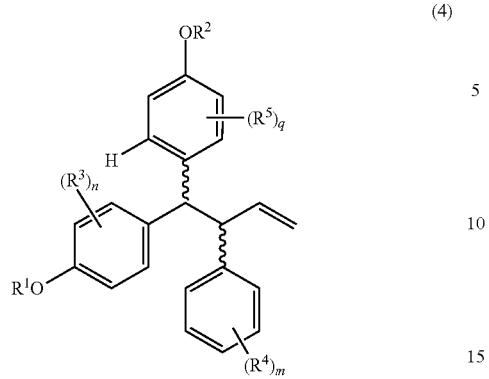

where, in the formula above, $R^1$ to $R^5$, n, m, and q are each the same as those described above; and the wave lines represent a bond of R or S configuration; and (b) preparing one of a compound expressed by the formula (5) below and a mixture of stereoisomers thereof by halogen-induced carbocyclization reaction of one of a compound expressed by the formula (4) and a mixture of stereoisomers thereof;

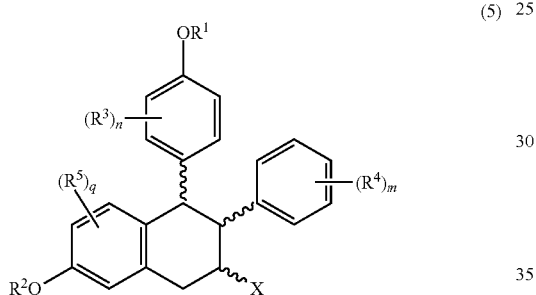

where, in the formula above, $R^1$ to $R^5$, n, m, and q are each the same as those described above; X represents a halogen atom; and the wave lines represent a bond of R or S configuration.

2. A method for producing a compound expressed by the formula (8), comprising affecting one of a compound expressed by the formula (5) or a mixture of stereoisomers thereof with at least one of an alcoholate and an amine salt to cause de-hydrogen halide, rearrangement of double bond, and elimination reaction of $R^1$ group to prepare a compound expressed by the formula (8) below,

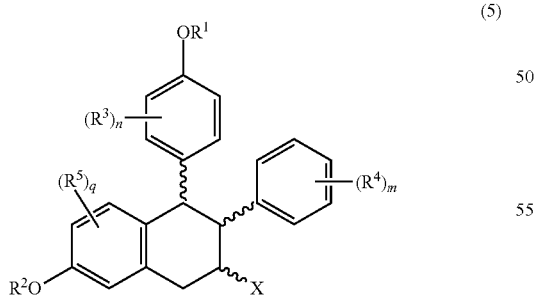

where, in the formula above, $R^1$ represents a hydrogen atom, an alkyl group, an acyl group, an alicyclic group, or an aromatic group; $R^2$ represents a hydrogen atom, an alkyl group, an acyl group, an alicyclic group, or an aromatic group; $R^3$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; $R^4$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; $R^5$ represents at least one substituent selected from a hydrogen atom, an alkyl group, an acyl group, an alicyclic group, an aromatic group, a halogen atom, a hydroxyl group, an alkyloxy group, and an acyloxy group; n represents an integer of 1 to 4; m represents an integer of 1 to 5; q represents an integer of 1 to 3; X represents a halogen atom; and the wave lines represent a bond of R or S configuration;

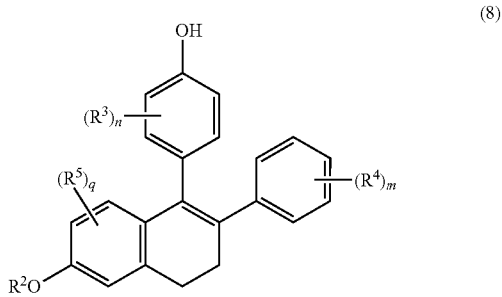

where, in the formula above, $R^2$ represents a hydrogen atom, an acyl group, an alicyclic group, or an aromatic group; $R^3$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; $R^4$ represents at least one substituent selected from a hydrogen atom, an alkyl group, an acyl group, an alicyclic group, an aromatic group, a halogen atom, an alkyloxy group, an acyloxy group, a cyano group, and a nitro group; $R^5$ represents at least one substituent selected from a hydrogen atom, an alkyl group, an acyl group, an alicyclic group, an aromatic group, a halogen atom, a hydroxyl group, an alkyloxy group, and an acyloxy group; n represents an integer of 1 to 4; m represents an integer of 1 to 5; q represents an integer of 1 to 3.

3. A compound expressed by formula (5) below or a mixture of stereoisomers thereof;

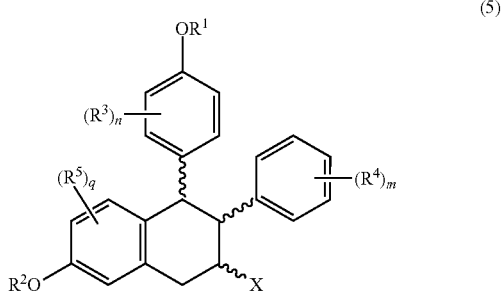

where, in the formula above, $R^1$ represents a hydrogen atom, an alkyl group, an acyl group, an alicyclic group, or an aromatic group; $R^2$ represents a hydrogen atom, an alkyl group, an acyl group, an alicyclic group, or an aromatic group; $R^3$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; $R^4$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; $R^5$ represents at least one substituent selected from a hydrogen atom, an alkyl group, an acyl group, an alicyclic group, an aromatic group, a halogen atom, a hydroxyl group, an alkyloxy group, and an acyloxy group; n represents an integer of 1 to 4; m represents an integer of 1 to 5; q represents an integer of 1 to 3; X represents a halogen atom; and the wave lines represent a bond of R or S configuration.

4. A compound expressed by the formula (8) below,

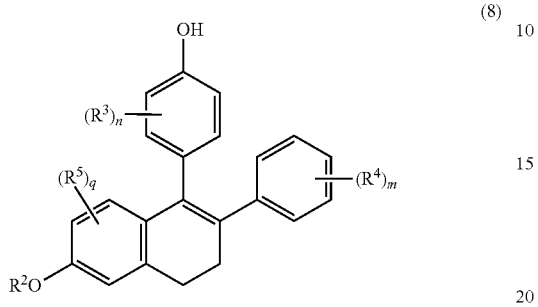
(8)

where, in the formula above, $R^2$ represents a hydrogen atom, an alkyl group, an acyl group, an alicyclic group, or an aromatic group, wherein the alkyl group is not a methyl group; $R^3$ represents at least one substituent selected from a hydrogen atom, an alkyl group, an acyl group, an alicyclic group, an aromatic group, a halogen atom, a hydroxyl group, an alkyloxy group, an acyloxy group, a cyano group, and a nitro group; $R^4$ represents at least one substituent selected from a hydrogen atom, an alkyl group, an acyl group, an alicyclic group, an aromatic group, a halogen atom, an alkyloxy group, an acyloxy group, a cyano group, and a nitro group; $R^5$ represents at least one substituent selected from a hydrogen atom, an alkyl group, an acyl group, an alicyclic group, an aromatic group, a halogen atom, a hydroxyl group, an alkyloxy group, and an acyloxy group; n represents an integer of 1 to 4; m represents an integer of 1 to 5; q represents an integer of 1 to 3.

* * * * *